United States Patent [19]

Sawai et al.

[11] Patent Number: 5,308,836
[45] Date of Patent: May 3, 1994

[54] PHARMACEUTICAL COMPOSITION OF STABILIZED [LEU$^{13}$]-MOTILIN-HSE

[75] Inventors: Kiichi Sawai; Masayasu Kurono; Yasuaki Kondo; Makoto Sato; Toshiyuki Kouzaki, all of Aichi, Japan

[73] Assignee: Sanwa Kagaku Kenkyusho Co., Ltd., Aichi, Japan

[21] Appl. No.: 116,682

[22] Filed: Sep. 7, 1993

Related U.S. Application Data

[63] Continuation of Ser. No. 863,251, Apr. 3, 1992.

[30] Foreign Application Priority Data

Apr. 9, 1991 [JP] Japan .................................. 3-076202
Mar. 12, 1992 [JP] Japan .................................. 4-087484

[51] Int. Cl.$^5$ ...................... A61K 37/24; A61K 37/36
[52] U.S. Cl. ........................................ 514/12; 514/13
[58] Field of Search ................................... 514/12, 13

[56] References Cited

U.S. PATENT DOCUMENTS 5,011,824  4/1991  Masada et al. .................. 514/12 X

FOREIGN PATENT DOCUMENTS 0437622  7/1991  European Pat. Off. .
341032A  2/1991  Japan .
341033A  2/1991  Japan .
380096A  4/1991  Japan .
3218395  9/1991  Japan .

Primary Examiner—Howard E. Schain
Attorney, Agent, or Firm—Nikado, Marmelstein, Murray & Oram

[57] ABSTRACT

There is disclosed a pharmaceutical composition of stabilized [Leu$^{13}$]-motilin-Hse. The composition comprises at least one of organic acids and salts thereof, as a first stabilizer, and pH thereof is adjusted in a range of 5.5–8.0. The composition may contain at least one of substances selected from saccharides, amino acids, proteins and salts thereof, as a second stabilizer. Conversion of [Leu$^{13}$]-motilin-Hse into [Leu$^{13}$]-motilin-Hse-lactone is suppressed by increasing pH value and deamidization in asparagine residue at 19-position is suppressed by the presence of the organic acid or salt thereof.

14 Claims, 6 Drawing Sheets

PHARMACEUTICAL COMPOSITION OF STABILIZED [LEU$^{13}$]-MOTILIN-HSE

This is a continuation of application Ser. No. 07/863,251 filed Apr. 3, 1992 pending.

BACKGROUND OF THE INVENTION

1. Field of the Invention

The present invention relates to a pharmaceutical composition of stabilized [Leu$^{13}$]-motilin-Hse.

2. Related Arts

Recent developments in chemical synthesis and biological application technologies make possible production of various proteins, peptides and others with desired biological activities.

A compound of [Leu$^{13}$-motilin-Hse has been developed by the present inventors as the substance showing biological activities similar to native motilin (this is one of peptide hormones and shows various biological activities, and more particularly an accelerating function of digestive canal) and having possibility of large scale production with use of biotechnology, through various studies and investigations on motilin and various motilin analogues [Jap. Pat. Nos. Hei 3-80096(A) and 3-218395(A)]. Structural differences of [Leu$^{13}$]-motilin-Hse from native type motilin lie in that methionine (Met) residue at 13-position of an amino acid sequence coded by the native type motilin is substituted with leucine (Leu) residue, and that homoserine (Hse) residue is added at C-terminal (23-position). When biotechnologies are applied for, the [Leu$^{13}$]-motilin-Hse can easily be prepared with a cost less than that for preparing the native type motilin and [Leu$^{13}$]-motilin and shows higher biological activities than the latters [said Jap. Pat. No. Hei 3-218395(A).

Similar to general biologically active peptides, the motilins are apt to be affected by various external factors such as heat, humidity, light beam, and peptidases and thus stored in a refrigerator. As measures for stabilizing the motilins, then, it has been proposed to prepare an aqueous solution containing the motilin and adjusted in pH of 4.0–5.5 or lyophilize the solution [Jap. Pat. No. Hei 3-41032(A)], and to prepare a solution containing the motilin and a stabilizer selected from amino acids and proteins, or lyophilize the solution [Jap. Pat. No. Hei 3-41033(A)].

In the Claims for said Jap. Pat. Nos. Hei 3-41032(A) and 41033(A), there is referred to "motilins" but actually stabilized motilins are native type motilin and [Leu$^{13}$]-motilin, only.

While, the motilin analogue of [Leu$^{13}$]-motilin-Hse has homoserine (Hse) residue at C-terminal (23-position) and thus it can not give a sufficient stability, even if pH shall be adjusted to 4.0–5.5, since there is such a possibility that the homoserine residue at 23-position shall change into lactone form in a pH range less than 5.5, even if the motilin analogue is kept in a state of aqueous solution or lyophilized powder.

The inventors have further found through studies and investigations on [Leu$^{13}$]-motilin-Hse that there is a possibility of deamidization or formation of cyclic imide in asparagine (Asp) residue at 19-position and it becomes a cause to reduce the stability of the motilin analogue, in question.

In other words, it is impossible to give a sufficient stabilization to the motilin analogue of [Leu$^{13}$]-motilin-Hse with pH adjustment only, in different from the native type motilin and [Leu$^{13}$]-motilin as teached in said Jap. Pat. No. Hei 3-41032(A).

It is preferable, further, that [Leu$^{13}$]-motilin-Hse shows its stability in neutral pH or pH range near thereto to reduce a stipulation, when it is administered through an injection.

SUMMARY OF THE INVENTION

A principal object of the invention is to provide a pharmaceutical composition of [Leu$^{13}$]-motilin-Hse by stabilizing the motilin analogue, so that the composition can be transported in ordinal conditions which require no reservation in a refrigerator.

The inventors have further energetically studied and investigated for developing the pharmaceutical composition of stabilized [Leu$^{13}$]-motilin-Hse and suitable for actual use to finally find out, surprisingly, that coexistence of an organic acid or salt thereof effectively exhibits the reaction of deamidization and formation of cyclic imide in asparagine residue at 19-position for [Leu$^{13}$]-motilin-Hse to establish the invention by combining this finding with the fact as referred to before, namely the finding that the homoserine residue at C-terminal shall change into lactone form in the pH range of 5.5 or more less.

According to the invention, therefore, the problems in the prior arts can be dissolved to attain the object by a pharmaceutical composition of stabilized [Leu$^{13}$]-motilin-Hse, which comprises an effective amount of [Leu$^{13}$]-motilin-Hse and at least one of substances of first stabilizer selected from the group consisting of organic acids and a salt thereof, and is adjusted in pH of 5.5–8.0.

The ground that the first stabilizer is defined as "at least one of substances selected from the group consisting of organic acids and a salt thereof" lies in that coexistence of an inorganic acid or salt thereof reduces a stability of [Leu$^{13}$]-motilin-Hse.

It has been found that further coexistence of at least one of substances selected from the group consisting of saccharides, amino acids and proteins to be conventionally used, mainly as a filer and additionally as a stabilizer for preparing a medicine comprising a biologically active peptide or protein serves to further stabilization of [Leu$^{13}$]-motilin-Hse. Therefore, the pharmaceutical composition according to the invention may contain such a substance, as a second stabilizer.

The [Leu$^{13}$]-motilin-Hse prepared by any process can be employed as the main ingredient for the pharmaceutical composition according to the invention, and without distinction of molecular type one, or a salt with an organic or inorganic acid.

As a pH adjusting reagent for preparing the pharmaceutical composition, any of them allowed for preparing medicines can be used, and followings may be listed; hydrochloric acid-sodium hydroxide, acetic acid-sodium acetate, glycine-sodium chloride-hydrochloric acid, potassium dihydrogenphosphate-disodium hydrogenphosphate, potassium hydrogenphthalate-sodium hydroxide, sodium secondary citrate-hydrochloric acid, sodium dihydrogenphosphate-disodium hydrogenphosphate, sodium dihydrogenphosphate-dipotassium hydrogenphosphate, potassium dihydrogenphosphate-dipotassium hydrogenphosphate, tartaric acid-sodium tartarate, lactic acid-sodium lactate, sodium barbital-sodium acetate-hydrochloric acid, succinic acid-boric acid, potassium primary citrate-sodium hydroxide, sodium primary citrate-borax, disodium hydrogenphosphate-citric acid, sodium acetate-hydrochloric acid, glutamic acid-sodium hydroxide, and aspartic acid-sodium hydroxide. Among them, hydrochloric acid-sodium hydroxide, acetic acid-sodium acetate, glycine-sodium chloride-hydrochloric acid, tartaric acid-sodium tartarate, lactic acid-sodium lactate, sodium acetate-hydrochloric acid, glutamic acid-sodium hydroxide, and aspartic acid-sodium hydroxide are preferable.

There is no specific limitation on the organic acid and salt thereof, which is used as the first stabilizer for preparing the pharmaceutical composition, if it shall be allowed from the view point of pharmaceutical preparation, and followings can be listed; formic acid, acetic acid, propionic acid, butyric acid, tartaric acid, valeic acid, caproic acid, caprylic acid, capric acid, lactic acid, oxalic acid, malonic acid, succinic acid, glutaric acid, adipic acid, maleic acid, fumalic acid, aspartic acid, glutamic acid, citric acid, as well as a salt thereof with an alkali metal. It is preferable, in general, to use the first stabilizer in an amount of 0.01-10000 parts by weight based on 1 part of [Leu$^{13}$]-motilin-Hse.

Use of an inorganic acid or salt thereof should be avoided, since it causes reduction of the stability of [Leu$^{13}$]-motilin-Hse. When an aqueous solution of [Leu$^{13}$]-motilin-Hse, wherein 200 mM potassium dihydrogenphosphate exists, and adjusted its pH in a range of 5.5-8.0 shall be stored at 60° C. for 30 days, for instance, a remaining amount of [Leu$^{13}$]-motilin-Hse becomes 58.9, 35.2, 21.7 or 5.3% in pH condition of 5.5, 6.5, 7.0 or 8.0, respectively.

As the saccharide among the second stabilizer which is eventually used for the preparation of the pharmaceutical composition according to the invention, any of them including monosaccharides, oligosaccharides, polysaccharides, or a derivative thereof, if it shall be allowed from view point as pharmaceutical preparations, and followings may be listed; glucose, sucrose, maltose, lactose, sugar alcohol (glycerin, inositol, mannitol, megrumine or the like), hyaluronic acid, a salt thereof, heparin, inulin, chitin and a salt thereof, dextran, dextrin (molecular weight: 3000-150000), as well as a derivative of polysaccharide and salt thereof [hydroxypropylcellulose (HPC), hydroxypropylmethylcellulose (HPMC), hydroxymethylcellulose (HMC), carboxymethylcellulose (CMC), and a salt thereof]. It is preferable, in general, to use the saccharide in an amount of 0.01-10000 parts by weight based on 1 part of [Leu$^{13}$]-motilin-Hse.

There is also no limitation on the amino acid among the second stabilizer, if it shall be allowed from view point as pharmaceutical preparations, and followings may be listed; alanine, leucine, isoleucine, proline, phenylalanine, tryptophan, serine, threonine, cysteine, asparagine, glutamine, lysine, arginine, and a salt thereof. It is preferable, in general, to use the amino acid in an amount of 0.01-10000 parts by weight based on 1 part of [Leu$^{13}$]-motilin-Hse.

There is also no limitation on the protein among the second stabilizer, if it shall be allowed from view point as pharmaceutical preparations, and followings may be listed; serum albumin, serum globurin, collagen, gelatin, gelatin treated with acid (molecular weight: 7000-100000), and gelatin treated with alkali. It is preferable, in general, to use the protein in an amount of 0.01-10000 parts by weight based on 1 part of [Leu$^{13}$]-motilin-Hse.

The pharmaceutical composition according to the invention can be diluted with a pharmaceutically acceptable filer. A powder prepared by dissolving [Leu$^{13}$]-motilin-Hse into a refined water under coexistence of 75 mM sodium aspartate or 75 mM tartaric acid 150 mM arginine, as well as 75 mM mannitol or 75 mM lactose, adjusting pH of the solution to 6.0 or 7.0, and lyophilizing the solution was stored at 60° C. for 30 days to measure a remaining amount of the motilin analogue to find that the amount is not different from that another powder just after the lyophilization and prepared without use the saccharides as the filer.

A form of medicine prepared with pharmaceutical composition according to the invention may be of a solid such as tablet, pill, capsule, powder or granule for oral dosage, suppository, or liquid of solution, suspension or emulsion for injectional or oral dosage. For preparing the medicine, one or more pharmaceutically acceptable substances selected from the followings can, of course, be used in response to a selected form of medicine; reserving agent, stabilizer, antioxidant, filer, binder, disintegrator, humectant, lubricant, coloring agent, flavour, taste modifier, emulsifier, isotonizing agent, agent for inhibiting pain and the like.

DETAILED DESCRIPTION OF THE PREFERRED EMBODIMENTS

Figure 1:
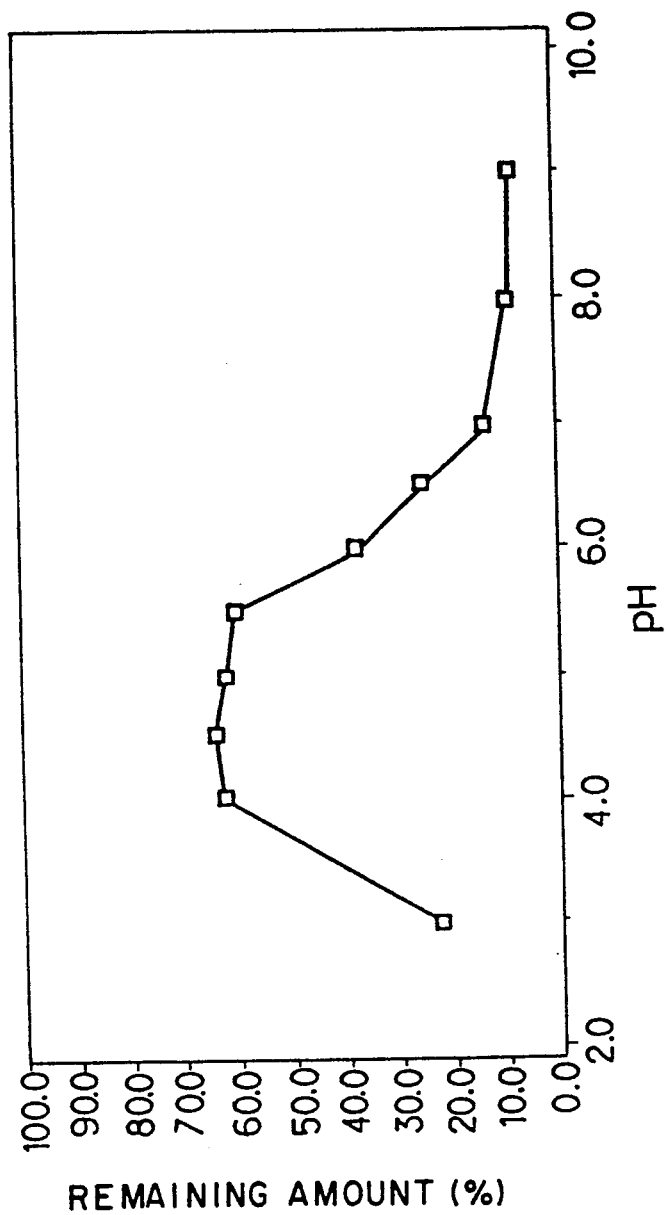
FIG. 1 is a graph showing a relation between a remaining amount of [Leu$^{13}$]-motilin and pH of its solution, when aqueous solutions of the motilin analogue different in pH value were prepared, and the remaining amount was measured after stored each solution at 60° C. for 30 days.

The invention will now be further explained in more detail with reference to Comparative Examples and Examples.

Comparative Example 1

An aqueous solution containing 20 μg/ml of [Leu$^{13}$]-motilin-Hse was aseptically prepared by dissolving 1 mg of [Leu$^{13}$]-motilin-Hse in a refined water and adding 0.1N-sodium hydroxide and 0.1N-hydrochloric acid to adjust pH of the solution to 6.0 or 7.0.

Each of the solutions different in pH value was aseptically charged in a glass vial to seal the same. Each vial was stored in a constant temperature bath kept at 60° C. for 30 days and then a remaining amount of [Leu$^{13}$]-motilin-Hse was measured with HPLC method.

Results are shown in Table 1 given later.

Comparative Example 2

An aqueous solution containing 20 μg of [Leu$^{13}$]-motilin-Hse and 34.8 mg/ml of arginine was aseptically prepared by dissolving 1 mg of [Leu$^{13}$]-motilin-Hse and arginine in a refined water and adding 0.1N-sodium hydroxide and 0.1N-hydrochloric acid to adjust pH of the solution to 6.0 or 7.0.

Each of the solutions different in pH value was aseptically charged in a glass vial to seal the same. Each vial was stored in a constant temperature bath kept at 60° C. for 30 days and then a remaining amount of [Leu$^{13}$]-motilin-Hse was measured with HPLC method.

Results are shown in Table 1 given later.

Example 1

An aqueous solution containing 20 μg of [Leu$^{13}$]-motilin-Hse and 30 mg/ml of tartaric acid was aseptically prepared by dissolving 1 mg of [Leu$^{13}$]-motilin-Hse and tartaric acid in a refined water and adding 0.1N-sodium hydroxide and 0.1N-hydrochloric acid to adjust pH of the solution to 6.0 or 7.0.

Each of the solutions different in pH value was aseptically charged in a glass vial to seal the same. Each vial was stored in a constant temperature bath kept at 60° C. for 30 days and then a remaining amount of [Leu$^{13}$]-motilin-Hse was measured with HPLC method.

Results are shown in following Table 1.

TABLE 1

| | Additive | Remaining amount (%)* pH 6.0 | pH 7.0 |
|---|---|---|---|
| Comparative Example 1 | — | 73.5 | 33.0 |
| Comparative Example 2 | Arginine | 64.7 | 40.9 |
| Example 1 | Tartaric acid | 73.5 | 71.0 |

In Table 1,
*Remaining amount of [Leu$^{13}$]-motilin-Hse.

It is apparent from the results shown in Table 1 that the motilin analogue causes a partial decomposition or modification in aqueous solution with higher pH value, and this phenomenon can not be sufficiently suppressed with coexistence of the amino acid but remarkably suppressed by coexistence of the organic acid.

Comparative Example 3

Aqueous solutions, each containing 20 μg/ml of [Leu$^{13}$]-motilin were aseptically prepared by dissolving 1 mg of [Leu$^{13}$]-motilin in a refined water and adding 0.1N-sodium hydroxide and 0.1N-hydrochloric acid to adjust pH of each solution in various values.

Each of the solutions different in pH value was aseptically charged in a glass vial to seal the same. Each vial was stored in a constant temperature bath kept at 60° C. for 30 days and then a remaining amount of [Leu$^{13}$]-motilin was measured with HPLC method to check the relation with the pH value of the solution.

Results are shown in following Table 2 and FIG. 1.

TABLE 2

| pH value | Remaining amount of [Leu$^{13}$]-motilin (%) |
|---|---|
| 3.0 | 22.6 |
| 4.0 | 62.8 |
| 4.5 | 64.1 |
| 5.0 | 62.3 |
| 5.5 | 60.7 |
| 6.0 | 37.8 |
| 6.5 | 25.6 |

TABLE 2-continued

| pH value | Remaining amount of [Leu$^{13}$]-motilin (%) |
|---|---|
| 7.0 | 13.4 |
| 8.0 | 9.1 |
| 9.0 | 8.0 |

It is apparent from the results shown in Table 2 that the motilin analogue ([Leu$^{13}$]-motilin) shows a relatively high stability by setting the pH value in a range of about 4.0–5.5 and this supports the disclosure given in Jap. Pat. No. Hei 3-41032(A) introduced in the preamble part of this specification.

Comparative Example 4

Aqueous solutions, each containing 20 μg/ml of [Leu$^{13}$]-motilin-Hse were aseptically prepared by dissolving 1 mg of [Leu$^{13}$]-motilin-Hse in a refined water and adding 0.1 N-sodium hydroxide and 0.1 N-hydrochloric acid to adjust pH of each solution in various values.

Each of the solutions different in pH value was aseptically charged in a glass vial to seal the same. Each vial was stored in a constant temperature bath kept at 60° C. for 30 days and then a remaining amount of [Leu$^{13}$]-motilin-Hse and amount of [Leu$^{13}$]-motilin-Hse-lactone formed by modification of Hse residue at 23-position of the former were measured with HPLC method to check the relation with the pH value of the solution.

Figure 2:
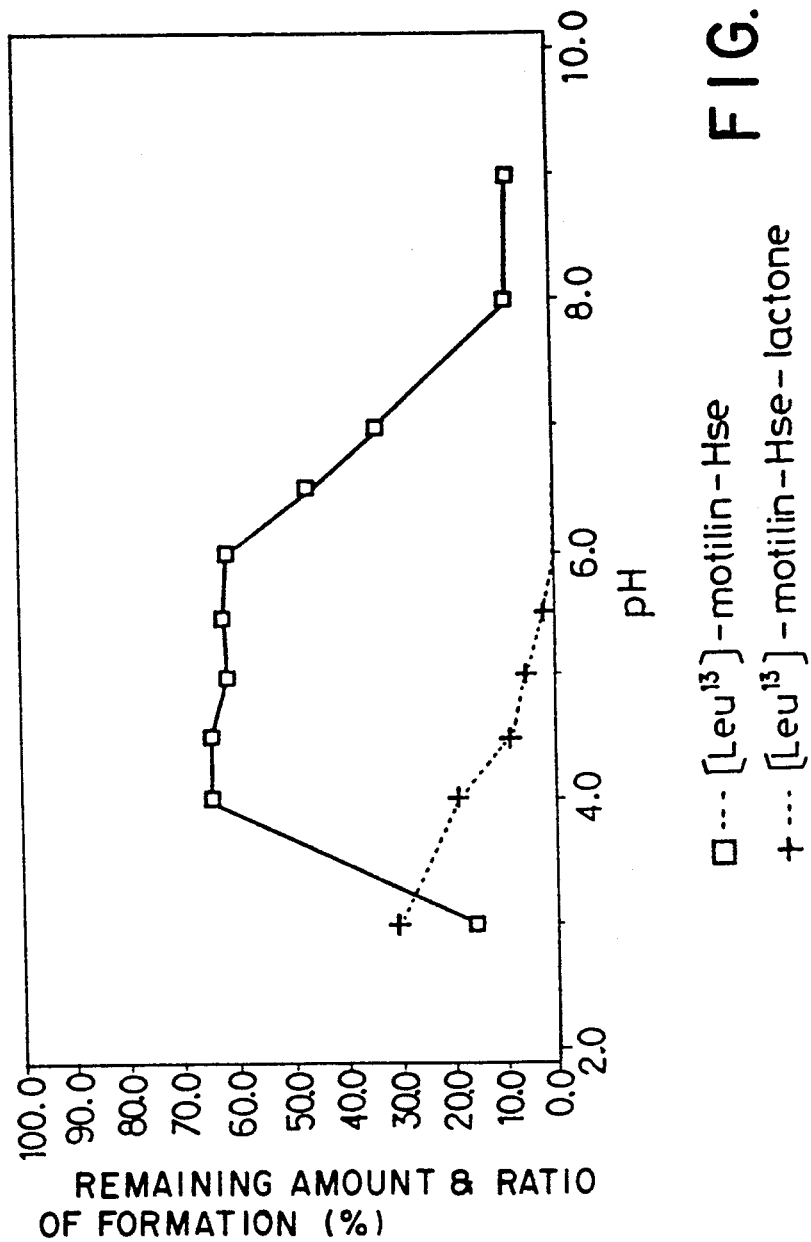
FIG. 2 is a graph showing a relation of a remaining amount of [Leu$^{13}$]-motilin-Hse, amount of formed [leu$^{13}$]-motilin-Hselactone and pH of its solution, when aqueous solutions of the motilin analogue different in pH value were prepared, and the the amounts were measured after stored each solution at 60° C. for 30 days.

Results are shown in following Table 3 and FIG. 2.

TABLE 3

| pH value | Remaining amount (%)* | Formed amount (%)** |
|---|---|---|
| 3.0 | 15.6 | 30.2 |
| 4.0 | 64.3 | 18.7 |
| 4.5 | 64.3 | 8.7 |
| 5.0 | 61.3 | 5.5 |
| 5.5 | 62.0 | 1.9 |
| 6.0 | 60.8 | 0 |
| 6.5 | 46.6 | 0 |
| 7.0 | 33.0 | 0 |
| 8.0 | 8.1 | 0 |
| 9.0 | 7.3 | 0 |

In Table 3,
*Remaining amount of [Leu$^{13}$]-motilin-Hse, and
**Amount of formed [Leu$^{13}$]-motilin-Hse-lactone.

It is apparent from results shown in Table 3 the motilin analogue ([Leu$^{13}$]-motilin-Hse) can also be kept in a relatively stable state by setting pH value of the solution in a range of about 4.0–6.0, but modification into [Leu$^{13}$]-motilin-Hse-lactone will occur in the pH range of 5.5 or more less.

Example 2

Aqueous solutions, each containing 20 μg/ml of [Leu$^{13}$]-motilin-Hse and 30 mg/ml of tartaric acid were aseptically prepared by dissolving 1 mg of [Leu$^{13}$]-motilin-Hse and tartaric acid in a refined water and adding 0.1 N-sodium hydroxide and 0.1 N-hydrochloric acid to adjust pH of each solution in various values.

Each of the solutions different in pH value was aseptically charged in a glass vial to seal the same. Each vial was stored in a constant temperature bath kept at 60° C. for 30 days and then a remaining amount of [Leu$^{13}$]-motilin-Hse and amount of [Leu$^{13}$]-motilin-Hse-lactone formed by modification of Hse residue at 23-position of the former were measured with HPLC method to check the relation with the pH value of the solution.

Figure 3:
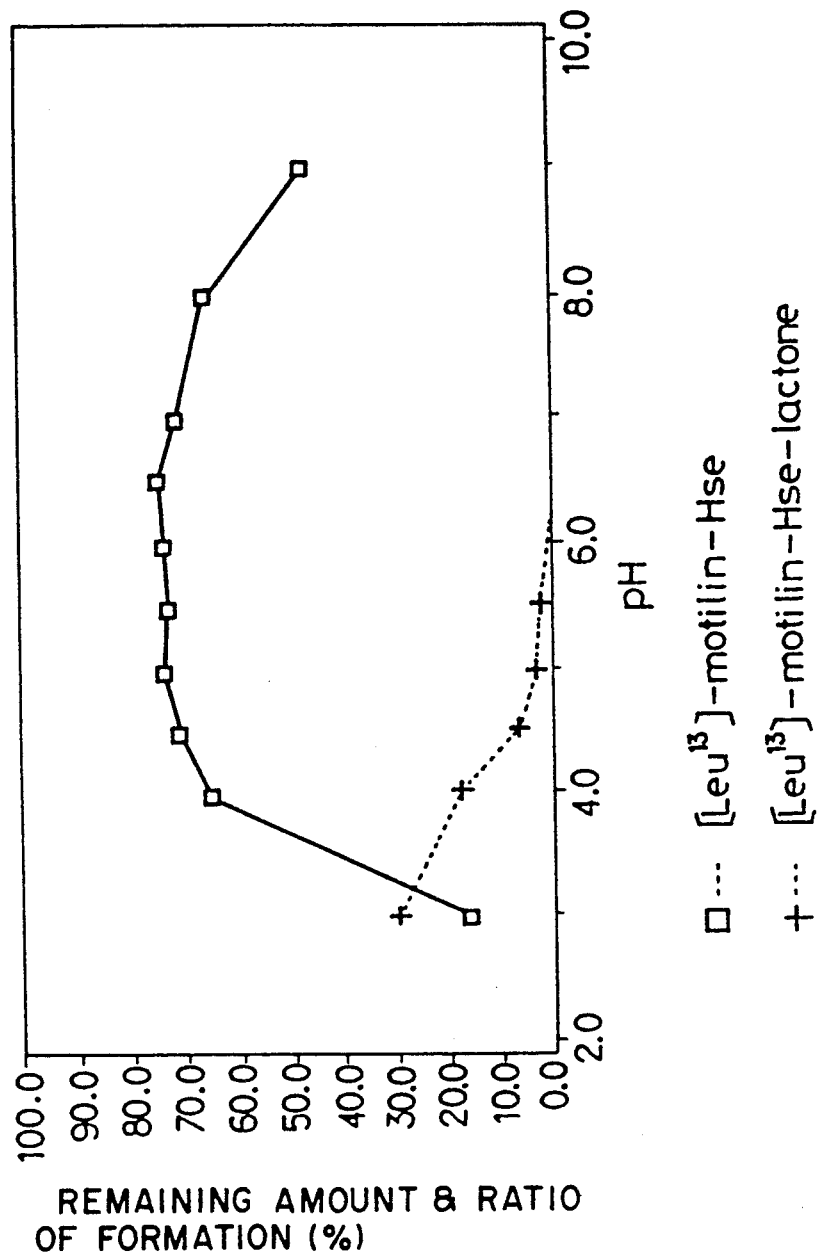
FIG. 3 is a graph similar to FIG. 2, but on a solution wherein tartaric acid was added.

Results are shown in following Table 4 and FIG. 3.

TABLE 4

| pH value | Remaining amount (%)* | Formed amount (%)** |
| --- | --- | --- |
| 3.0 | 15.8 | 29.7 |
| 4.0 | 65.3 | 16.8 |
| 4.5 | 70.7 | 6.4 |
| 5.0 | 73.6 | 2.7 |
| 5.5 | 72.8 | 1.5 |
| 6.0 | 73.5 | 0 |
| 6.5 | 74.1 | 0 |
| 7.0 | 71.0 | 0 |
| 8.0 | 65.3 | 0 |
| 9.0 | 45.9 | 0 |

In Table 4,
*Remaining amount of [Leu$^{13}$]-motilin-Hse, and
**Amount of formed [Leu$^{13}$]-motilin-Hse-lactone It is apparent from the results shown in Table 4 that in case of the motilin analogue ([Leu$^{13}$]-motilin-Hse), a pH range wherein the motilin analogue shows a stability expands to about 4.0–8.0, by adding the organic acid and the formation of [Leu$^{13}$]-motilin-Hse-lactone can be suppressed by setting pH value of the solution higher than 5.5.

Comparative Example 5

Aqueous solutions, each containing 20 μg/ml of [Leu$^{13}$]-motilin-Hse and 27.2 mg/ml of potassium dihydrogenphosphate were aseptically prepared by dissolving 1 mg of [Leu$^{13}$]-motilin-Hse and potassium dihydrogenphosphate in a refined water and adding 0.1 N sodium hydroxide and 0.1 N-hydrochloric acid to adjust pH of each solution in various values.

Each of the solutions different in pH value was aseptically charged in a glass vial to seal the same. Each vial was stored in a constant temperature bath kept at 60° C. for 30 days and then a remaining amount of [Leu$^{13}$]-motilin-Hse and amount of [Leu$^{13}$]-motilin-Hse-lactone formed by modification of Hse residue at 23-position of the former were measured with HPLC method to check the relation with the pH value of the solution.

Figure 4:
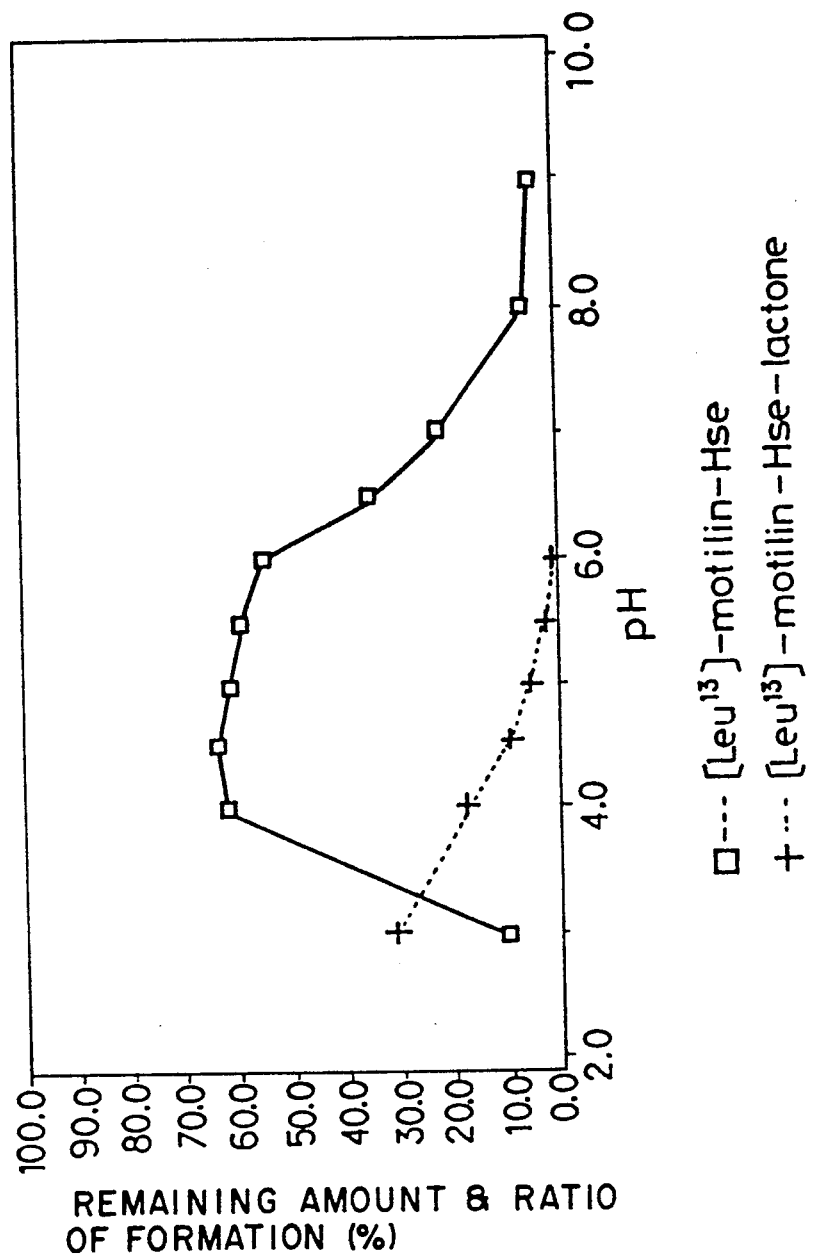
FIG. 4 is a graph similar to FIG. 2, but on a solution wherein potassium dihydrogenphosphate was added.

Results are shown in following Table 5 and FIG. 4.

TABLE 5

| pH value | Remaining amount (%)* | Formed amount (%)** |
| --- | --- | --- |
| 3.0 | 10.1 | 31.1 |
| 4.0 | 61.8 | 17.5 |
| 4.5 | 63.4 | 9.3 |
| 5.0 | 60.9 | 5.7 |
| 5.5 | 58.9 | 2.1 |
| 6.0 | 55.1 | 0 |
| 6.5 | 35.2 | 0 |
| 7.0 | 21.7 | 0 |
| 8.0 | 5.3 | 0 |
| 9.0 | 4.1 | 0 |

In Table 5,
*Remaining amount of [Leu$^{13}$]-motilin-Hse, and
**Amount of formed [Leu$^{13}$]-motilin-Hse-lactone.

It is apparent from the results shown in Table 5 that the motilin analogue ([Leu$^{13}$]-motilin-Hse) shows a relatively high stability in lower pH range, when the inorganic acid coexists, but in such lower pH range, the formation rate of [Leu$^{13}$]-motilin-Hse-lactone increases, so that the existence of the inorganic acid gives bad influence, when the motilin analogue should be stored under conditions with higher pH range.

Comparative Example 6

Aqueous solutions, each containing 20 μg/ml of [Leu$^{13}$]-motilin were aseptically prepared by dissolving 1 mg of [Leu$^{13}$]-motilin in a refined water and adding 0.1N-sodium hydroxide and 0.1N-hydrochloric acid to adjust pH of each solution in various values.

Each of the solutions different in pH value was aseptically charged in a glass vial to lyophilize the same. Each vial was stored in a constant temperature bath kept at 60° C. for 30 days and then a remaining amount of [Leu$^{13}$]-motilin was measured with HPLC method to check the relation with the pH value of the solution.

Figure 5:
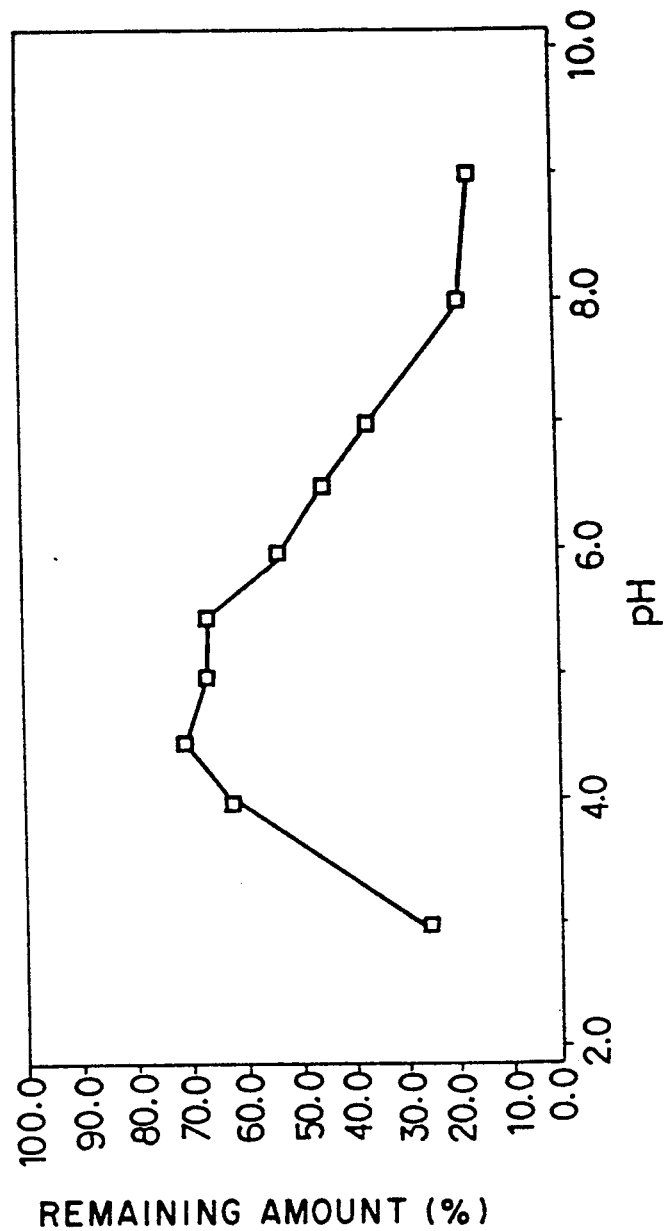
FIG. 5 is a graph similar to FIG. 1, but on lyophilized powder which was prepared by freeze-drying the aqueous solution of [Leu$^{13}$]-motilin.

Results are shown in following Table 6 and FIG. 5.

TABLE 6

| pH value | Remaining amount of [Leu$^{13}$]-motilin (%) |
| --- | --- |
| 3.0 | 25.6 |
| 4.0 | 62.5 |
| 4.5 | 70.4 |
| 5.0 | 66.3 |
| 5.5 | 65.6 |
| 6.0 | 52.7 |
| 6.5 | 44.1 |
| 7.0 | 35.8 |
| 8.0 | 17.8 |
| 9.0 | 15.3 |

It is apparent from the results shown in Table 6 that it is preferable to lyophilize the solution prepared by setting its pH value to about 4.0–5.5, and that the lyophilized powder is more stable than the aqueous solution, by comparing the results with those given in Comparative Example 3 (Table 2, FIG. 1).

Comparative Example 7

Aqueous solutions, each containing 20 μg/ml of [Leu$^{13}$]-motilin-Hse were aseptically prepared by dissolving 1 mg of [Leu$^{13}$]-motilin-Hse in a refined water and adding 0.1N-sodium hydroxide and 0.1N-hydrochloric acid to adjust pH of each solution in various values.

Each of the solutions different in pH value was aseptically charged in a glass vial to lyophilize the same. Each vial was stored in a constant temperature bath kept at 60° C. for 30 days and then a remaining amount of [Leu$^{13}$]-motilin-Hse and amount of [Leu$^{13}$]-motilin-Hse-lactone formed by modification of Hse residue at 23-position of the former were measured with HPLC method to check the relation with the pH value of the solution.

Figure 6:
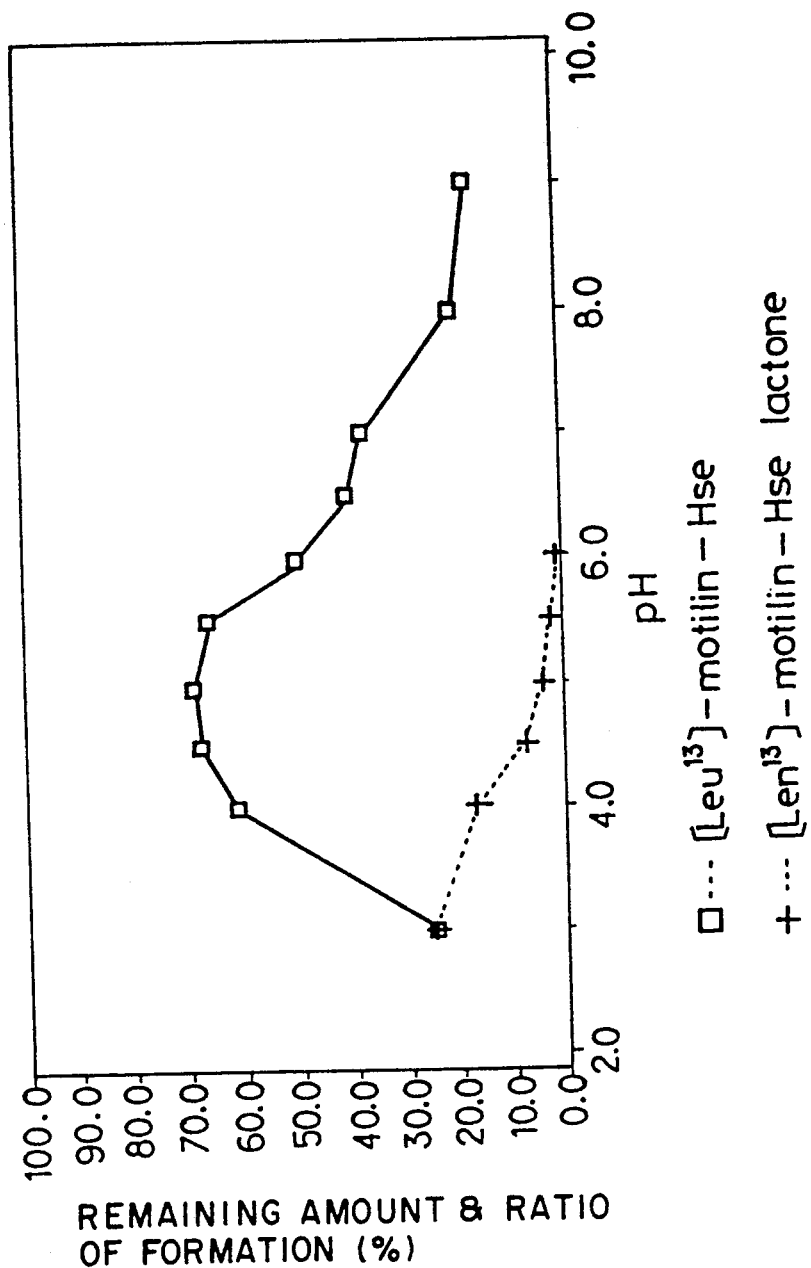
FIG. 6 is a graph similar to FIG. 2, but on lyophilized powder which was prepared by freeze-drying the aqueous solution of [Leu$^{13}$]-motilin-Hse.

Results are shown in following Table 7 and FIG. 6.

TABLE 7

| pH value | Remaining amount (%)* | Formed amount (%)** |
| --- | --- | --- |
| 3.0 | 24.4 | 25.1 |
| 4.0 | 61.8 | 16.9 |
| 4.5 | 67.0 | 7.3 |
| 5.0 | 68.5 | 3.9 |
| 5.5 | 65.7 | 1.8 |
| 6.0 | 49.3 | 0 |
| 6.5 | 40.0 | 0 |
| 7.0 | 37.6 | 0 |
| 8.0 | 20.3 | 0 |
| 9.0 | 16.8 | 0 |

In Table 7,
*Remaining amount of [Leu$^{13}$]-motilin-Hse, and
**Amount of formed [Leu$^{13}$]-motilin-Hse-lactone.

It is apparently seen from the results shown in Table 7 that the motilin analogue ([Leu$^{13}$]-motilin-Hse) shows a relatively high stability in a pH range of about 4.0–5.5, but [Leu$^{13}$]-motilin-Hse-lactone will be formed in the pH range of 5.5 or more less, and the amount thereof is somewhat less than that in the liquid state. This means that sufficient stability of [Leu$^{13}$]-motilin-Hse can not be secured by lyophilization only.

Example 3-6 and Comparative Example 8

Aqueous solutions, each containing 20 μg/ml of [Leu$^{13}$]-motilin-Hse and a following additive were aseptically prepared by dissolving 1 mg of [Leu$^{13}$]-motilin-Hse and the additive in a refined water and adding 0.1N-sodium hydroxide and 0.1N-hydrochloric acid to adjust pH of each solution to 6.0 or 7.0.

Each of the solutions was aseptically charged in a glass vial to lyophilize the same. Each vial was stored in a constant temperature bath kept at 60° C. for 30 days and then a remaining amount of [Leu$^{13}$]-motilin-Hse and amount of deamide compound which was formed by modification of asparagine (Asn) residue at 19-position of the motilin analogue ([Leu$^{13}$]-motilin-Hse) were measured with HPLC method to check the relation with the pH value of the solution.

|  | Additive | Concentration (mg/ml) |
|---|---|---|
| Control | — | — |
| Comparative Example 8 | KH$_2$PO$_4$ | 27.2 |
| Example 3 | Asp (Na) | 31.0 |
| Example 4 | Tartaric acid | 30.0 |
| Example 5 | Sodium acetate | 16.4 |
| Example 6 | Sodium lactate | 22.4 |

Results are shown in following Table 8.

TABLE 8

|  | Remaining amount (%)* | | Formed amount (%)** | |
|---|---|---|---|---|
|  | pH 6.0 | pH 7.0 | pH 6.0 | pH 7.0 |
| Control | 49.3 | 37.6 | 50.2 | 60.9 |
| Comp. Ex. 8 | 35.2 | 28.5 | 63.1 | 69.8 |
| Example | | | | |
| 3 | 94.1 | 93.8 | 5.8 | 6.0 |
| 4 | 93.8 | 93.2 | 6.0 | 6.5 |
| 5 | 92.1 | 91.8 | 7.8 | 8.2 |
| 6 | 91.9 | 91.2 | 8.0 | 8.5 |

In Table 8,
*Remaining amount of [Leu$^{13}$]-motilin-Hse,
**Amount of formed deamide compound.

As apparent from the results shown in Table 8, it has been found that the organic acid and salt thereof effectively suppress the modification in asparagine residue at 19-position in about neutral pH range to stabilize the motilin analogue ([Leu$^{13}$]-motilin-Hse), and while, co-existence of the inorganic acid unstabilize the motilin analogue.

Comparative Example 9-16

Aqueous solutions, each containing 20 μg/ml of [Leu$^{13}$]-motilin-Hse and an additive (following saccharide or amino acid) were aseptically prepared by dissolving 1 mg of [Leu$^{13}$]-motilin-Hse and the additive in a refined water, and adding 0.1N-sodium hydroxide and 0.1N-hydrochloric acid to adjust pH of each solution to 6.0 or 7.0.

Each of the solutions was aseptically charged in a glass vial to lyophilize the same. Each vial was stored in a constant temperature bath kept at 60° C. for 30 days and then a remaining amount of [Leu$^{13}$]-motilin-Hse and amount of deamide compound which was formed by modification of asparagine (Asn) residue at 19-position of the motilin analogue ([Leu$^{13}$]-motilin-Hse) were measured with HPLC method to check the relation with the pH value of the solution.

|  | Additive | Concentration (mg/ml) |
|---|---|---|
| Control | — | — |
| Comparative Example | | |
| 9 | Mannitol | 36.4 |
| 10 | Inositol | 36.0 |
| 11 | Lactose | 68.5 |
| 12 | Maltose | 68.5 |
| 13 | Dextran 70 | 50.0 |
| 14 | Glycine | 15.0 |
| 15 | Alanine | 17.8 |
| 16 | Arginine | 34.8 |

Results are shown in following Table 9.

TABLE 9

|  | Remaining amount (%)* | | Formed amount (%)** | |
|---|---|---|---|---|
|  | pH 6.0 | pH 7.0 | pH 6.0 | pH 7.0 |
| Control | 49.3 | 37.6 | 50.2 | 60.9 |
| Comp. Example | | | | |
| 9 | 50.3 | 39.3 | 48.7 | 58.9 |
| 10 | 67.5 | 65.8 | 30.8 | 34.0 |
| 11 | 64.7 | 63.9 | 35.0 | 35.2 |
| 12 | 65.3 | 62.9 | 34.2 | 35.7 |
| 13 | 88.7 | 88.8 | 11.0 | 11.0 |
| 14 | 62.8 | 58.1 | 36.3 | 40.3 |
| 15 | 59.7 | 53.6 | 38.5 | 45.2 |
| 16 | 96.0 | 95.7 | 3.8 | 4.1 |

In Table 9,
*Remaining amount of [Leu$^{13}$]-motilin-Hse,
**Amount of formed deamide compound.

As apparent from the results shown in Table 9, it has been found that excepting arginine, the amino acid or saccharide per se can not sufficiently suppress the formation of deamide compound. In connection with this, please note that the results shown in Table 9 are on lyophilized powder, and that, in case of existing arginine in the solution, the remaining amount of [Leu$^{13}$]-motilin-Hse is 64.7% (pH 6.0) or 40.9% (pH 7.0) (see Comparative Example 2, Table 1).

Example 7-12 and Comparative Example 17

Aqueous solutions, each containing 20 μg/ml of [Leu$^{13}$]-motilin-Hse and following additive(s) were aseptically prepared by dissolving 1 mg of [Leu$^{13}$]-motilin-Hse and the additive(s) in a refined water, and adding 0.1N-sodium hydroxide and 0.1N-hydrochloric acid to adjust pH of each solution to 6.0 or 7.0.

Each of the solutions was aseptically charged in a glass vial to lyophilize the same. Each vial was stored in a constant temperature bath kept at 60° C. for 30 days and then a remaining amount of [Leu$^{13}$]-motilin-Hse and amount of deamide compound which was formed by modification of asparagine (Asn) residue at 19-position of the motilin analogue ([Leu$^{13}$]-motilin-Hse) were measured with HPLC method to check the relation with the pH value of the solution.

Control:
No additive,
Comparative Example 17:
KH$_2$PO$_4$ (13.6 mg/ml) + Arg (34.8 mg/ml),
Example 7:
Asp Na (15.5 mg/ml) + Arg (34.8 mg/ml),
Example 8:
Asp Na (11.6 mg/ml) + Arg (26.1 mg/ml) + Mannitol (13.7 mg/ml),
Example 9:
Asp Na (11.6 mg/ml) + Arg (26.1 mg/ml) + Lactose (25.7 mg/ml), Example 10:
Tartaric acid (15.0 mg/ml)+Arg (34.8 (mg/l),
Example 11:
Tartaric acid (11.3 mg/ml)+Arg (26.1 mg/ml)+Mannitol (13.7 mg/ml), and
Example 12:
Tartaric acid (11.3 mg/ml)+Arg (26.1 mg/ml)+Lactose (25.7 mg/ml).

TABLE 10

|  | Remaining amount (%)* | | Formed amount (%)** | |
|---|---|---|---|---|
|  | pH 6.0 | pH 7.0 | pH 6.0 | pH 7.0 |
| Control | 96.0 | 95.7 | 3.8 | 4.1 |
| Comp. Ex. 17 | 89.2 | 87.8 | 10.5 | 12.0 |
| Example |  |  |  |  |
| 7 | 99.9 | 98.7 | 0 | 1.1 |
| 8 | 100.9 | 97.9 | 0 | 1.8 |
| 9 | 99.5 | 98.3 | 0 | 0.5 |
| 10 | 100.2 | 101.3 | 0 | 0 |
| 11 | 99.8 | 99.7 | 0 | 0 |
| 12 | 102.0 | 99.8 | 0 | 0 |

In Table 10,
*Remaining amount of [Leu$^{13}$]-motilin-Hse,
**Amount of formed deamide compound.

As apparent from the results shown in Table 10, the stability of [Leu$^{13}$]-motilin-Hse can be increased, when the amino acid, or amino acid and saccharide coexist(s), in addition to an organic acid or salt thereof.

What is claimed is:

1. A method of stabilizing [Leu$^{13}$]-motilin-[Hse$^{23}$] comprising the steps of
   adding a first stabilizer selected from the group consisting of formic acid, acetic acid, propionic acid, butyric acid, tartaric acid, valeic acid, caproic acid, caprylic acid, capric acid, lactic acid, oxalic acid, malonic acid, succinic acid, glutaric acid, adipic acid, maleic acid, fumalic acid, citric acid and salts thereof, and
   adjusting the pH to between 5.5-8.0.

2. The method according to claim 1, wherein the first stabilizer is added in an amount necessary to achieve a concentration of 0.01-10000 parts by weight based on 1 part of said [Leu$^{13}$]-motilin-[Hse$^{23}$].

3. The method according to claim 1, further comprising the addition of at least one secondary stabilizer selected from the group consisting of saccharide, amino acids, proteins, and salts thereof.

4. The method according to claim 3, wherein the secondary stabilizer is added in an amount necessary to achieve a concentration of 0.01-10000 parts by weight based on 1 part of [Leu$^{13}$]-motilin-[Hse$^{23}$].

5. The method according to claim 3, wherein said saccharide is selected from the group consisting of glucose, sucrose, maltose, lactose, glycerin, inositol, mannitol, megrumine, hyaluronic acid, heparin, inulin, chitin, dextran, dextrin, hydroxypropylcellulose, hydroxypropylmethylcellulose, hydroxymethylcellulose and carboxymethylcellulose.

6. The method according to claim 3, wherein said amino acid is selected from the group consisting of alanine, leucine, isoleucine, proline, phenylalanine, tryptophan, serine, threonine, cysteine, asparagine, glutamine, lysine and arginine.

7. The method according to claim 3, wherein said protein is selected from the group consisting of serum albumin, serum globulin, collagen, gelatin, gelatin treated with acid and gelatin treated with alkali.

8. A pharmaceutical composition of stabilized [Leu$^{13}$]-motilin-[Hse$^{23}$], comprising an effective amount of [Leu$^{13}$]-motilin-[Hse$^{23}$] and at least one stabilizer selected from the group consisting of formic acid, acetic acid, propionic acid, butyric acid, tartaric acid, valeic acid, caproic acid, caprylic acid, capric acid, lactic acid, oxalic acid, malonic acid, succinic acid, glutaric acid, adipic acid, maleic acid, fumalic acid, citric acid and salts thereof, wherein said pharmaceutical composition has a pH between 5.5-8.0.

9. A pharmaceutical composition as claimed in claim 8, wherein an amount of said first stabilizer occupies 0.01-10000 parts by weight based on 1 part of said [Leu$^{13}$]-motilin-Hse.

10. A pharmaceutical composition as claimed in claim 8, further comprising at least one of substances of second stabilizer selected from the group consisting of saccharides, amino acids, proteins, and a salt thereof.

11. A pharmaceutical composition as claimed in claim 10, wherein an amount of said second stabilizer occupies 0.01-10000 parts by weight based on 1 part of said [Leu$^{13}$]-motilin-Hse.

12. A pharmaceutical composition as claimed in claim 10, wherein said saccharide is selected from the group consisting of glucose, sucrose, maltose, lactose, glycerin, inositol, mannitol, megrumine, hyaluronic acid, heparin, inulin, chitin, dextran, dextrin, hydroxypropylcellulose, hydroxypropylmethylcellulose, hydroxymethylcellulose, and carboxymethylcellulose.

13. A pharmaceutical composition as claimed in claim 10, wherein said amino acid is selected from the group consisting of alanine, leucine, isoleucine, proline, phenylalanine, tryptophan, serine, threonine, cysteine, asparagine, glutamine, lysine, and arginine.

14. A pharmaceutical composition as claimed in claim 10, wherein said protein is selected from the group consisting of serum albumin, serum globurin, collagen, gelatin, gelatin treated with acid, and gelatin treated with alkali.

* * * * *